(12) United States Patent
Gunday et al.

(10) Patent No.: US 10,463,232 B2
(45) Date of Patent: Nov. 5, 2019

(54) ANCHORED GUIDEWIRE

(71) Applicant: Sanovas Intellectual Property, LLC, Reno, NV (US)

(72) Inventors: Erhan H. Gunday, Great Neck, NY (US); Lawrence J. Gerrans, San Anselmo, CA (US)

(73) Assignee: Sanovas Intellectual Property, LLC, Reno, NV (US)

( * ) Notice: Subject to any disclaimer, the term of this patent is extended or adjusted under 35 U.S.C. 154(b) by 0 days.

(21) Appl. No.: 16/267,080

(22) Filed: Feb. 4, 2019

(65) Prior Publication Data

US 2019/0167076 A1 Jun. 6, 2019

Related U.S. Application Data

(62) Division of application No. 12/906,736, filed on Oct. 18, 2010, now abandoned.

(51) Int. Cl.
*A61B 1/00* (2006.01)
*A61B 1/015* (2006.01)
(Continued)

(52) U.S. Cl.
CPC .......... *A61B 1/00082* (2013.01); *A61B 1/01* (2013.01); *A61B 1/015* (2013.01); *A61B 5/6851* (2013.01);
(Continued)

(58) Field of Classification Search
CPC ....... A61B 1/00082; A61B 1/01; A61B 1/015; A61B 5/6851; A61B 5/6882; A61B 5/6876; A61M 25/09
See application file for complete search history.

(56) References Cited

U.S. PATENT DOCUMENTS 4,207,872 A 6/1980 Meiri et al.
5,059,176 A 10/1991 Viinters
(Continued)

FOREIGN PATENT DOCUMENTS

WO 2008042347 A2 4/2008

OTHER PUBLICATIONS

International Search Report & Written Opinion of the International Searching Authority; Application No. PCT/US2011/056510; dated Jan. 11, 2012; dated Feb. 1, 2012; 10 pages. (submitted in parent U.S. Appl. No. 12/906,736).

(Continued)

*Primary Examiner* — Timothy J Neal
(74) *Attorney, Agent, or Firm* — Forge IP, PLLC

(57) ABSTRACT

An anchored guide wire is described including at least one expansion apparatus having an outer surface for contacting surrounding tissue, an elongated guide wire with at least one lumen for supplying fluid to the expansion apparatus, and a pump that supplies fluid to the lumen to inflate the expansion apparatus, wherein the outer surface of the expansion apparatus has a textured surface for preventing slippage on surrounding tissue. A method of securing a guide wire in a bodily cavity is also described including inserting an elongated guide wire with an expansion apparatus having a textured outer surface and a lumen for supplying fluid to the expansion apparatus, into the bodily cavity, supplying fluid to the lumen with a pump until the expansion apparatus is inflated, moving a medical device along the elongated guide wire, deflating the expansion apparatus, and withdrawing the guide wire from the bodily cavity.

20 Claims, 14 Drawing Sheets

(51) Int. Cl.
*A61B 5/00* (2006.01)
*A61M 25/09* (2006.01)
*A61B 1/01* (2006.01)

(52) U.S. Cl.
CPC ........... *A61M 25/09* (2013.01); *A61B 5/6876* (2013.01); *A61B 5/6882* (2013.01)

(56) References Cited

U.S. PATENT DOCUMENTS

| | | | |
|---|---|---|---|
| 5,167,239 A | 12/1992 | Cohen et al. | |
| 5,209,727 A | 5/1993 | Radisch, Jr. et al. | |
| 5,269,759 A * | 12/1993 | Hernandez | A61M 25/09 600/585 |
| 5,423,745 A | 6/1995 | Todd et al. | |
| 5,484,412 A | 1/1996 | Pierpont | |
| 5,499,995 A | 3/1996 | Teirstein | |
| 5,693,014 A | 12/1997 | Abele et al. | |
| 5,720,726 A | 2/1998 | Marcadis et al. | |
| 5,938,585 A | 8/1999 | Donofrio | |
| 6,110,192 A | 8/2000 | Ravenscroft et al. | |
| 6,544,276 B1 | 4/2003 | Azizi | |
| 6,585,639 B1 * | 7/2003 | Kotmel | A61B 1/00082 600/114 |
| 6,932,828 B2 | 8/2005 | Bonnette et al. | |
| 6,936,056 B2 | 8/2005 | Nash et al. | |
| 6,942,678 B2 | 9/2005 | Bonnette et al. | |
| 6,986,778 B2 | 1/2006 | Ladno-Azizi | |
| 7,008,438 B2 | 3/2006 | O'Brien | |
| 7,513,886 B2 | 4/2009 | Konstantino | |
| 7,615,031 B2 | 11/2009 | Bonnette et al. | |
| 7,744,620 B2 | 6/2010 | Pedersen et al. | |
| 7,914,487 B2 | 3/2011 | Davies, Jr. et al. | |
| 8,226,601 B2 | 7/2012 | Gunday et al. | |
| 2001/0041874 A1 | 11/2001 | Reydel | |
| 2004/0230219 A1 | 11/2004 | Roucher, Jr. | |
| 2004/0243224 A1 | 12/2004 | Tremble | |
| 2005/0080357 A1 | 4/2005 | Eberhart et al. | |
| 2005/0159645 A1 | 7/2005 | Bertolero et al. | |
| 2005/0273050 A1 | 12/2005 | Yokoyama et al. | |
| 2005/0288551 A1 | 12/2005 | Callister et al. | |
| 2006/0015038 A1 | 1/2006 | Weymarn-Scharli | |
| 2006/0178560 A1 | 8/2006 | Saadat et al. | |
| 2007/0083111 A1 | 4/2007 | Hossack et al. | |
| 2007/0142771 A1 | 6/2007 | Durcan | |
| 2007/0244431 A1 | 10/2007 | Limon | |
| 2008/0171985 A1 | 7/2008 | Karakoca | |
| 2008/0300618 A1 | 12/2008 | Gertner | |
| 2009/0076447 A1 | 3/2009 | Casas et al. | |
| 2009/0287051 A1 | 11/2009 | Itoi | |
| 2009/0326631 A1 | 12/2009 | Drake et al. | |
| 2010/0004506 A1 | 1/2010 | Saadat | |
| 2010/0121270 A1 | 5/2010 | Gunday et al. | |
| 2010/0318029 A1 | 12/2010 | Pepper et al. | |
| 2011/0004058 A1 | 1/2011 | Oneda et al. | |
| 2012/0095292 A1 | 4/2012 | Gunday et al. | |
| 2012/0123327 A1 | 5/2012 | Miller | |
| 2012/0226103 A1 | 9/2012 | Gunday et al. | |
| 2012/0253120 A1 | 10/2012 | Callister et al. | |
| 2013/0116549 A1 | 5/2013 | Gunday et al. | |

OTHER PUBLICATIONS

International Search Report and Written Opinion of the International Searching Authority Application No. PCT/US2013/074620 Completed: Feb. 17, 2014; dated Mar. 10, 2014 13 pages. (submitted in parent U.S. Appl. No. 12/906,736).

* cited by examiner

ANCHORED GUIDEWIRE

FIELD OF THE INVENTION

The present invention relates to systems and methods for anchoring a guide wire in a patient's body during deployment and/or use of surgical instruments and devices. More specifically, the present invention relates to a guide wire with an expansion apparatus for securing the guide wire at a desired location and orientation for precise and minimally traumatic insertion and positioning of catheters, surgical instruments, devices and implants in bodily cavities.

BACKGROUND OF THE INVENTION

In modern medical practice, there is extensive use of various types of catheters, instruments, devices and implants for various medical procedures. The medical science is increasingly adopting minimally invasive technologies to address and remedy various pathologies and disease states affecting the human body. One of the advantages of such minimally invasive technologies is that they can be done through smaller keyhole incisions, stab punctures and/or through natural orifices of the body into cavities and vessels in the body. Such methods are intended to mitigate trauma to the body and to expedite patient recovery.

Various medical instruments, devices and implants that are transported into and out of the body through these minimally invasive incisions are typically small in diameter, linear and, consequently, can be difficult to guide and navigate into, through, and out of the body. The medical community has long used guide wires to address the difficulties of exacting the location and placement of medical instruments, devices and implants.

Coring, reaming, cutting and dilation devices, such as drills, reamers, dilators, taps, shears, energy delivery tools and similar instruments, are often guided into a desired position over a guide wire to open or create new passages into the body. Imaging devices such as cameras, scopes, probes and illumination fibers have been known to be placed over guide wires. Implants, such as stents, bone screws, intra-medullar rods, soft tissue anchors, valves and various other implants are commonly placed over guide wires. Commonly, the tubular structures of the body are intervened with devices known as catheters that are placed and delivered over guide wires.

A catheter is typically a hollow flexible tube for insertion into a body cavity, duct, or vessel to allow the passage of fluids or distend a passageway. Catheters thereby allow drainage, injection of fluids, or access by surgical instruments. The process of inserting a catheter is called catheterization. Often, a catheter is a thin, flexible tube ("soft" catheter). A catheter left inside the body, either temporarily or permanently, may be referred to as an indwelling catheter. A permanently inserted catheter may be referred to as a permcath. The three major types of catheters are coronary, renal, and infusion catheters. Other types of catheters exist for broad applications such as drainage, administration of fluids, measurement of pressures, circulation, etc.

Coronary catheters are used for procedures that involve insertion through a blood vessel into the heart for diagnostic and treatment purposes. For example, coronary catheters are commonly used for angiography procedure, which involves taking x-rays of blood vessels after injection of a radiopaque substance. Other common uses of the coronary catheters are angioplasty procedures that involve altering the structure of a vessel, placing stents, deploying valves and performing ultrasound and related diagnostic and treatment imaging studies in the heart or in peripheral veins and arteries.

Renal catheters are typically used for drainage of urine from the bladder through the urethra. A well-known type of renal catheters are Foley catheters, which are equipped with an inflatable balloon at the tip and are used for urine incontinence, terminal patients, and bladder drainage following surgery or an incapacitating injury or illness.

Infusion catheters are used for therapeutic introduction of a fluid, such as saline solution, into a body cavity or a vessel. In contrast to injection, infusion catheters allow for the introduction of a larger volume of a less concentrated solution over a more prolonged period of time.

Different catheter tips or guide devices may be used to guide a catheter to a target site within a patient's body. Often the target site is buried within a soft tissue, such as a brain or liver, and can be reached only by a convoluted pass through small vessels or ducts in the tissue. The difficulty in accessing such regions is that the catheter must be flexible in order to follow the convoluted pass into the tissue and at the same time stiff enough to allow the distal end of the catheter to be manipulated from an external access site.

Two general methods for the introduction of catheters have been commonly used. The first method employs a highly flexible catheter having a dilated distal end. A major limitation of this method is that the catheter will only travel in the path of highest blood flow rate, and therefore, many target sites with low blood flow rates cannot be accessed. Another limitation is that the dilated distal end makes it difficult to introduce the catheter through very small vessels or ducts without causing damage to the surrounding tissue.

In the second prior art method, a flexible guide wire having a distal bend is guided by alternatively rotating and advancing the wire to the target site. With the wire in place, a thin-walled catheter is then advanced along the wire until the distal catheter end is positioned at the target site. Once the catheter is advanced, the guide wire may be withdrawn to allow fluid delivery or withdrawal through the catheter. However, one of the disadvantages of this prior art method is that it is often very difficult to accurately position the catheter in a desired location within the patient's body, as the guide wire will often move away from the target site during the insertion of the catheter. Yet another limitation is that, because of the linear translation and/or rotational forces exerted upon the catheter during its insertion, translation and/or removal from its intended location, the guide wire may migrate from its original location and/or back out of the operative site altogether through the lumen of the catheter.

There have been some attempts to overcome the problems of know guide wire devices. For example, U.S. Pat. No. 5,167,239 to Cohen et al. describes an anchorable guidewire for use in various medical applications having an elongate guidewire body with an inflatable anchoring member or balloon and a deactuatable check valve positioned on the body for maintaining inflation of the balloon. The balloon is inflated via a syringe connected to a hub on the guidewire body.

However, the guide wire disclosed in Cohen et al. still suffers from a number of disadvantages and shortcomings. One of the most significant problems is that the guide wire of Cohen et al. may still migrate from the desired location during the insertion of the catheter. This is because the only securing mechanism holding the guide wire of Cohen et al. in place is the contact between the inflated balloon and surrounding cavity walls. The balloon described in Cohen et al. has a smooth surface, thereby making it prone to slippage during the insertion process, especially due to linear and/or rotational forces exerted upon the guide wire during the insertion of the catheter.

Another problem with the guide wire device disclosed in Cohen et al. is that it is rather complex and bulky, which makes it unsuitable for use in bodily cavities having a very small diameter. Additionally, the device of Cohen et al. is constructed with expensive materials, and therefore has to be reused multiple times, which requires complex sterilization procedures.

Yet another deficiency of the guide wire of Cohen et al. is that it is not able to be positioned as optimally as may be desired. For example, the guide wire of Cohen et al. does not provide a direct visual feedback of the area ahead, behind, and around the guide wire to optimize positioning of the guide wire. Further, the guide wire does not include material for externally identifying its position, such as a radio-opaque material. Therefore, one is not able to easily identify the position of the balloon via an external imaging modality, such as radiographic or ultrasonic imaging. Each of these shortcomings contributes to one's inability to position the guide wire as precisely as may be desired.

A further deficiency of the guide wire of Cohen et al. is that it lacks the capability to precisely gauge the size of the environment in which it is being used to provide physiological measurements and feedback that could aid precise and secure positioning of the guide wire. For example, there is no way for the surgeon to know the intra-lumen diameter of the bodily cavity in which the guide wire is to be secured, and no way to accurately adjust for changes in this diameter as the guide wire is moved within the cavity. Because it has no mechanism for measuring the intra-lumen diameter at different points within the cavity, one is not able to properly adjust the amount of pressure supplied to the anchoring balloon and thereby prevent slippage or migration of the balloon.

What is desired, therefore, is an improved guide wire device that addresses the dislocation, migration and instability problems of known guide wire devices. What is also desired is a guide wire that allows for more precise and minimally traumatic introduction, translation and/or removal of a catheter, instrument, device, implant or the like into, through, and out of the body.

SUMMARY OF THE INVENTION

It is, therefore, an object of the invention to provide a new and improved catheter guide wire that overcomes the problems of known devices.

In order to achieve at least the above-mentioned objects of the present invention, an anchored guide wire is provided including at least one expansion apparatus having an outer wall, the outer wall comprising an outer surface for contacting surrounding tissue, an elongated guide wire having at least one lumen therein for supplying fluid to the at least one expansion apparatus, and a pump that supplies fluid to the lumen to inflate the at least one expansion apparatus. The outer surface of the expansion apparatus comprises a textured surface for preventing slippage of said outer surface on the surrounding tissue.

In some embodiments, the guide wire further includes an imaging device disposed in the lumen. In some of these embodiments, the elongated guide wire includes an imaging device aperture, the imaging device has a distal end, and the distal end of the imaging device exits the aperture for viewing surrounding tissue. In certain embodiments, the imaging device aperture is positioned inside the at least one expansion apparatus, and the outer wall of the at least one expansion apparatus is transparent for viewing surrounding tissue via the imaging device. In some embodiments, the imaging device comprises a fiber optic bundle. In further embodiments, the imaging device comprises a flexible tip.

In certain embodiments, the elongated guide wire has a distal end comprising a transparent membrane, and the imaging device extends to the membrane for viewing tissue in front of the guide wire.

In other embodiments, the elongated guide wire has an opening at a distal end, and the imaging device extends out of the opening for viewing tissue in front of the guide wire. In some of these embodiments, the opening includes a cleaning device affixed to an inner surface of the guide wire for cleaning the imaging device.

In some embodiments, the at least one expansion apparatus comprises an inflatable balloon. In certain embodiments, the textured surface of the at least one expansion apparatus includes a mesh affixed to the outer wall of the apparatus. Similarly, in certain embodiments, the outer wall of the at least one expansion apparatus includes a plurality of inflatable cavities that provide the textured surface.

In certain advantageous embodiments, the fluid is a gas. In other advantageous embodiments, the pump is an electropneumatic pump. In certain embodiments, the pump further includes a vacuum source that evacuates the fluid from the at least one expansion apparatus.

In certain embodiments, the at least one expansion apparatus includes a plurality of segments, and the at least one lumen includes a plurality of lumens through which the pump supplies fluid to the plurality of segments such that the pump inflates at least one of the segments separately from at least one other of the segments. In some of these embodiments, at least one of the segments has two open ends to allow passage of external fluid through the at least one expansion apparatus.

In some embodiments, the at least one expansion apparatus includes at least one imaging marker. In some of these embodiments, the at least one imaging marker is a radio-opaque ring.

In certain embodiments, the elongated guide wire has a distal tip with an opening therein, and the elongated guide wire further includes a second inner lumen connected to the opening to allow fluids or instruments to be passed through the distal tip of the anchored guide wire.

In some advantageous embodiments, a check valve is positioned at a proximal end of the elongated guide wire for maintaining the at least one expansion apparatus in an inflated position, wherein an outer diameter of the check valve is the same as an outer diameter of the elongated guide wire.

In certain embodiments, the pump includes at least one sensor for measuring at least one parameter and a processor that controls the supply of the fluid based on at least one measured parameter. In some embodiments, the guide wire further includes a port positioned at a proximal end of the elongated guide wire for connection to the pump.

In some cases, the guide wire includes a plurality of expansion apparatuses positioned at different locations along the elongated guide wire.

The invention also comprises an anchored guide wire including an elongated guide wire having a proximal end and a distal end, an expansion apparatus positioned at the distal end of the elongated guide wire and having an outer wall, the outer wall comprising an outer surface for contacting tissue, wherein the elongated guide wire has a lumen therein for supplying fluid to the expansion apparatus, a pump that supplies fluid to the lumen to inflate the expansion apparatus, a check valve positioned at the proximal end of the elongated guide wire for maintaining the expansion apparatus in an inflated position. The outer surface of the expansion apparatus has a textured surface for preventing slippage of the outer surface on surrounding tissue. An outer diameter of the check valve is the same as an outer diameter of the elongated guide wire.

In some embodiments, the anchored guide wire further includes an imaging device disposed in the lumen.

A method of securing a guide wire in a bodily cavity is also described including the steps of inserting an elongated guide wire, which includes an expansion apparatus having a textured outer surface and a lumen for supplying fluid to the expansion apparatus, into the bodily cavity until the expansion apparatus reaches an anchoring position, supplying fluid to the lumen with a pump until the expansion apparatus is inflated such that the textured surface exerts sufficient pressure on the wall of the bodily cavity to retain the expansion apparatus in the anchoring position, moving a medical device along the elongated guide wire through the bodily cavity while the expansion apparatus is inflated until the medical device reaches a desired position, deflating the expansion apparatus, and withdrawing the guide wire from the bodily cavity.

In some embodiments, the pump includes at least one sensor for measuring at least one parameter and a processor for controlling the supply of fluid based on at the least one measured parameter.

In certain embodiments, the elongated guide wire has a check valve positioned at a proximal end thereof to maintain the inflation of the expansion apparatus, and wherein the step of deflating the expansion apparatus comprises disabling the check valve to release fluid from the expansion apparatus.

In some embodiments, the step of moving the medical device along the elongated guide wire comprises sliding a catheter over the elongated guide wire.

In certain embodiments, the method further includes the step of using an imaging device disposed in the lumen to visualize tissue in the bodily cavity. In some of these embodiments, the step of using an imaging device includes extending a distal tip of the imaging device through an aperture positioned inside the expansion apparatus, wherein the outer wall of the expansion apparatus is transparent. Similarly, in some of these embodiments the imaging device has a flexible tip. In further of these embodiments, the step of using an imaging device includes visualizing tissue in front of the guide wire via the imaging device through a transparent membrane positioned at a distal end of the elongated guide wire. In yet other of these embodiments, the step of using an imaging device includes extending a distal tip of the imaging device through an opening at a distal end of the elongated guide wire to visualize tissue in front of the guide wire. In these embodiments, the method further includes the step of cleaning the imaging device via a cleaning device positioned in the opening at the distal end of the elongated guide.

In some advantageous embodiments, the expansion apparatus is an inflatable balloon.

In certain embodiments, the method also includes the step of using at least one imaging marker to position the expansion apparatus within the bodily cavity.

In some embodiments, the expansion apparatus has a distal tip with an opening therein and the elongated guide wire has a second lumen connected to said opening, and the method further includes the step of passing a bodily fluid through the second opening and out the second lumen of the guide wire.

In certain embodiments, the expansion apparatus includes a plurality of segments, the elongated guide wire includes a plurality of lumens, and the step of supplying fluid to the expansion apparatus includes supplying fluid to the plurality of segments such that at least one of the segments is inflated separately from at least one other of the segments.

These and other objects, advantages and features of this invention will become apparent upon review of the following specification in conjunction with the drawings.

DETAILED DESCRIPTION OF THE INVENTION

Figure 1:
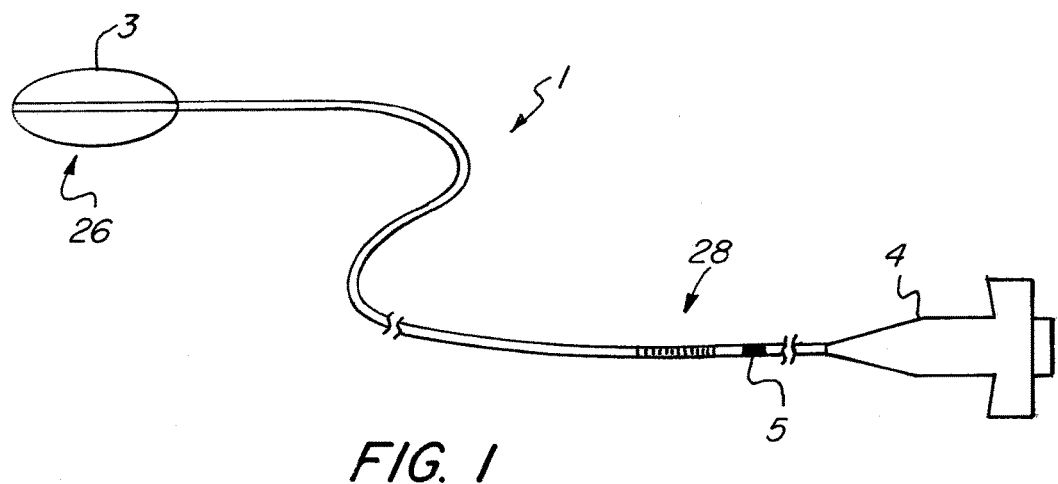
FIG. 1 is schematic view of an anchored guide wire in accordance with the invention.

The basic components of one embodiment of an anchored guide wire in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The anchored guide wire of the present invention may be used with various catheter devices, surgical instruments and tools, operative devices, implants and related medical diagnostic and treatment systems necessitating guidance over a guide wire type construct. In an advantageous embodiment, the anchored guide wire is used with a resector balloon system described in U.S. patent application Ser. No. 12/269, 495, the disclosure of which is incorporated by reference herein in its entirety.

As shown in FIG. 1, the anchored guide wire (1) includes an elongated guide wire (2) having a distal end (26) and a proximal end (28). The guide wire (2) may have any suitable diameter and length depending on a particular application, and may be flexible, rigid or semi rigid. The guide wire (2) may be made with any commercially available material that is flexible enough to allow it to be safely inserted through the available opening of a bodily cavity such that it will bend instead of puncturing the walls of the cavity. In an advantageous embodiment shown in FIG. 3, the guide wire (2) consists of a coil wire (30) made of any suitable material, such as stainless steel, and a coating (32) made of polyethylene.

The elongated guide wire (2) may include calibrated markings to aid visualization, measurement, and navigation of catheters, instruments, devices, implants and medical systems as they are positioned over, or through, the guide wire.

The elongated guide wire (2) has an outer diameter and an inner diameter. The outer diameter is preferably smaller than the inner diameter of the catheter with which it is used in order to allow for easy advancement of the catheter over the guide wire (2) during the insertion of the catheter into the body. The guide wire has a coating made of suitable smooth material to facilitate the movement of the guide wire through the bodily cavities and to facilitate insertion of the catheter.

The distal end of the elongated guide wire (2) includes at least one expansion apparatus (3) in a form of an inflatable balloon, which has an outer wall with a textured surface texture, when inflated, grips the bodily tissue, such as blood vessel walls. In should be understood that the expansion apparatus (3) may be constructed as any suitable inflatable device, such as an inflatable balloon, umbrella, wafer, anchor or a similar device. The expansion apparatus (3) may be made of latex, YULEX (biomaterial made from Guayule (*Parthenium argentatum*)), polyethylene, nylon or other suitable material, and may come in a variety of sizes and diameters, which allow the guide wire (1) to be used in bodily cavities of various diameters and dimensions.

Figure 2:
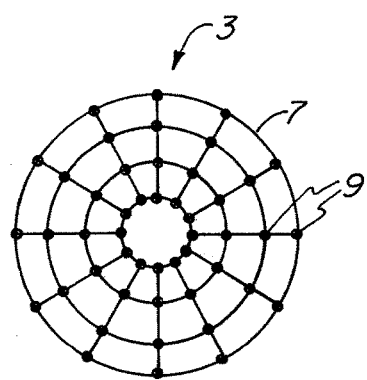
FIG. 2 is an end, partially cross-sectional view of the inflated balloon of the guide wire of FIG. 1.
Figure 18:
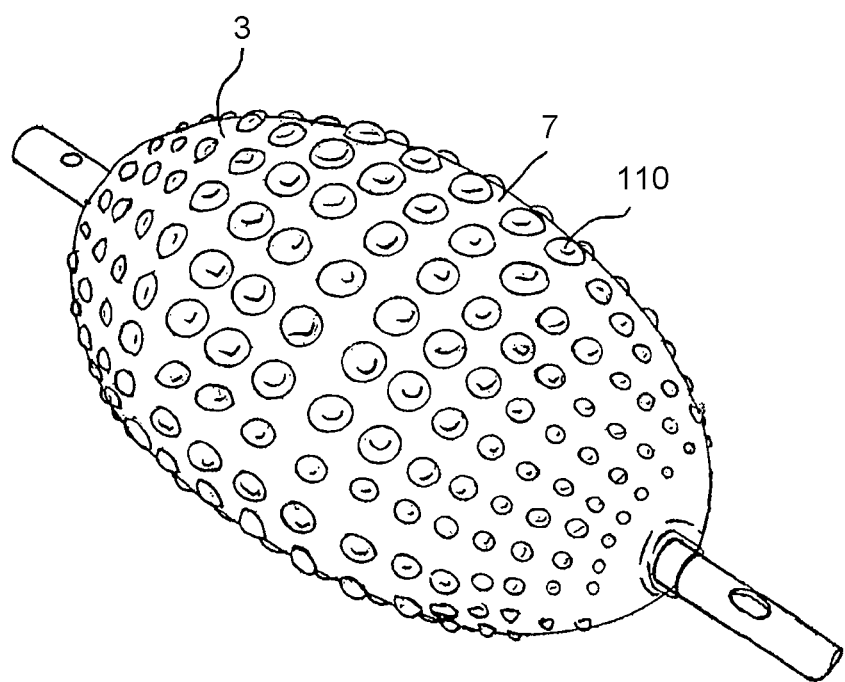
FIG. 18 is an enlarged perspective view of the inflated balloon of the guide wire of FIG. 1.

FIG. 2 illustrates an end view of the inflated balloon (3) of the anchored guide wire (1). The outer surface (7) of the balloon (3) includes a fiber mesh affixed to the surface of the balloon during the molding process, which produces outwardly-facing protrusions (9) on the surface of the balloon (3) that assist in gripping of the balloon to the surrounding tissue. The fiber mesh may be made of lycra, polyurethane, composite springs, or other appropriate material. In other embodiments, such as shown in FIG. 18, dimensional surface structures or inflatable sinuses (110) that are encapsulated in the surface substrate of the balloon (3) may be used to produce the surface protrusions.

In certain advantageous embodiments, the balloon (3) includes imaging markers, such as radio opaque rings, located at or near the ends thereof. Such markers can be selected and appropriately positioned in order to reflect or block the relevant waves of various imaging modalities (e.g., x-ray) in order to allow the use of such modalities to assist with the precise positioning of the balloon (3).

Figure 16:
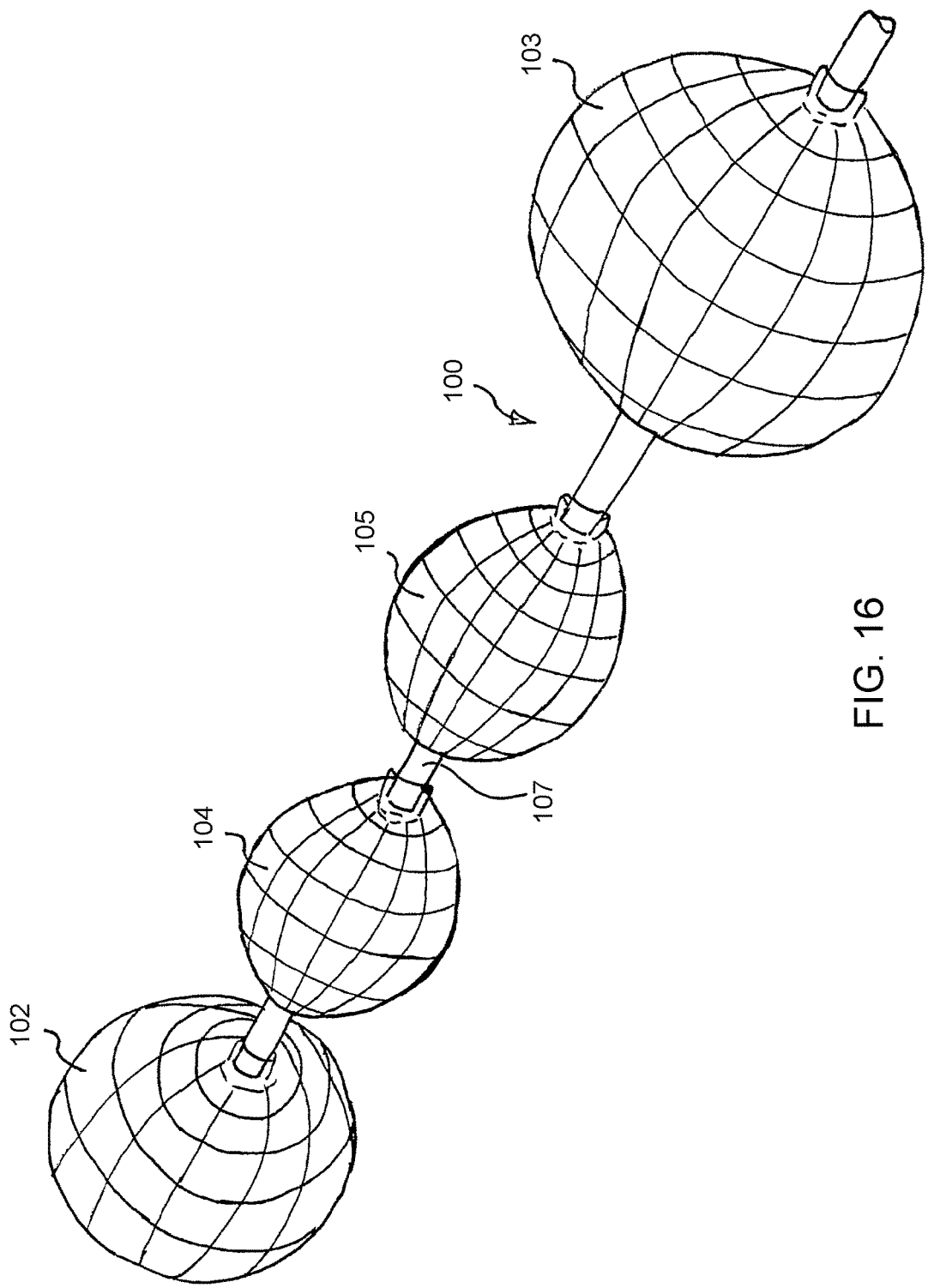
FIG. 16 is an enlarged perspective view of the guide wire of FIG. 1 with a plurality of expansion apparatuses.

It should be understood that the guide wire may also include a plurality of expansion apparatuses positioned at different locations along the elongated guide wire (2). For example, as shown in FIG. 16, the guide wire (100) includes a plurality of expansion apparatuses (102, 103, 104, 105) positioned along the elongated body (107) of the guide wire. Any number of expansion apparatuses may be used in accordance with the present invention. The plurality of expansion apparatuses allow for more precise and secure anchoring of the guide wire within the bodily cavity.

In addition to serving as an anchoring device to secure the guide wire within the bodily cavity, the expansion apparatus (es) (3) can also be used to block or prevent fluids from flowing around the expansion apparatus(es) of the target bodily lumen, vessel, airway or space.

Referring back to FIG. 1, the proximal end of the elongated guide wire (2) includes a port (4) for connection of the guide wire (1) to a fluid source, such as a pump, through which the balloon (3) is inflated. The port (4) is provided with any suitable connector, such as a luer connector, for connection to the pump.

Figure 8:
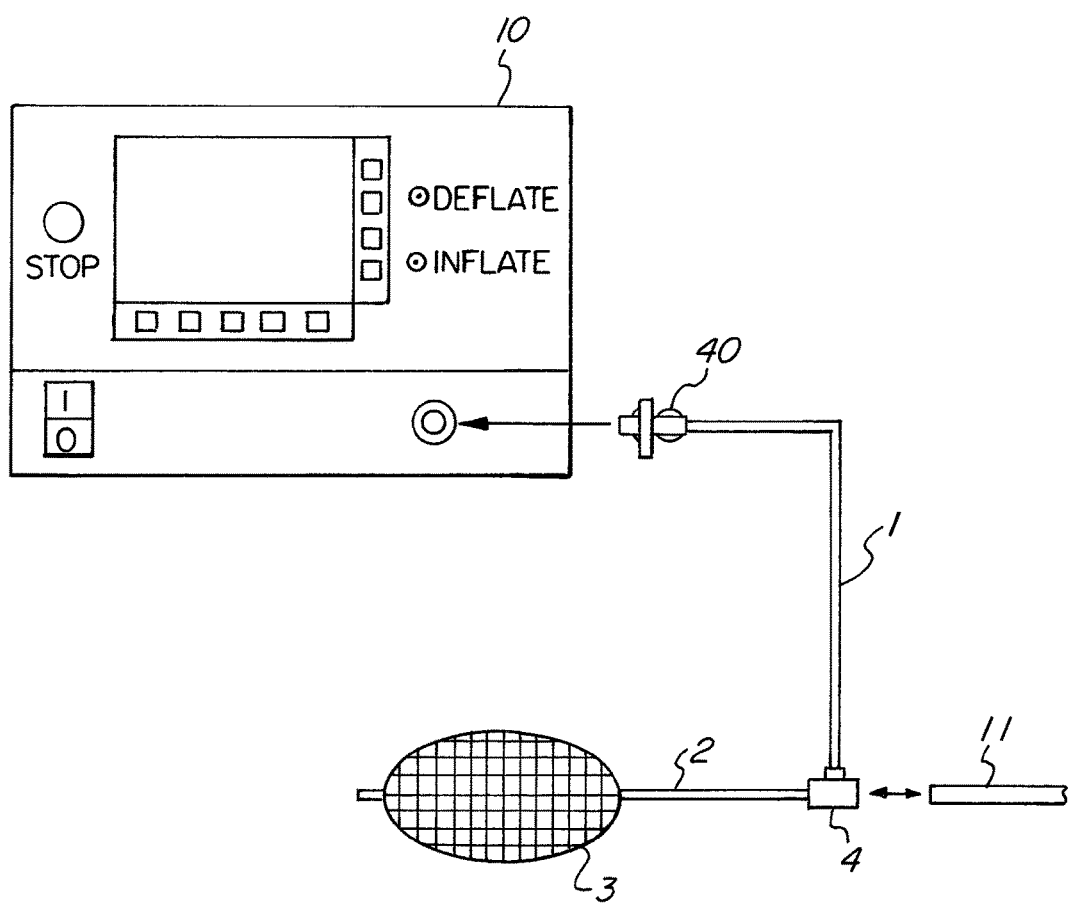
FIG. 8 is a partially schematic view of the guide wire of FIG. 1, showing connection to a pump.

The anchored guide wire (1) with the attached pump (10) is further shown in FIG. 8. The pump (10) supplies a fluid, such as a gas, liquid, or mixture thereof, to the balloon (3) via an inner lumen provided in the elongated guide wire (2) and is attached to the anchored guide wire (1) through a connector (40). Any suitable pump type may be used in accordance with the present invention. In a preferred embodiment, an electro-pneumatic pump is used, capable of controlling the amount of balloon inflation based on various predetermined or measured factors, such as a diameter of a bodily cavity into which the guide wire in introduced.

The pump (10) preferably includes a compressor and a fluid tank. The fluid pressure in the tank is continuously monitored by a microcontroller provided with the pump (10). Any suitable known type of the microcontroller may be used in accordance with the present invention. The microcontroller initiates the compressor to operate via an electrical signal output. In another variation of the pump (10), the pressurized fluid is instead provided from an external source, such as gas tank or the operating room walls commonly found in an operating room. In certain embodiments, a vacuum source is also included in the pump (10). The vacuum source is turned on and off by the microcontroller via an electrical output signal. The vacuum source is used to evacuate the fluid from the balloon (3) to facilitate faster deflation of the balloon. In some embodiments, the pump is capable of automatically identifying the anchored guide wire (type, size, etc.) and its characteristics when connected.

The pump (10) further includes a processor that controls the supply of fluid to the inflatable balloon (3) based on at least one predetermined parameter. In some embodiments, such predetermined parameters may be manually entered by the user. Alternatively, the control of the fluid is based on default parameters selected by the pump (10), which are based on the characteristics of the particular balloon and/or the diameter measurements of a particular bodily cavity made by the pump.

Once the anchored guide wire (1) is inserted into a desired position within the bodily cavity, the balloon (3) positioned at the distal end is inflated via the pump, and then the inflation port (4) is removed from the guide wire (2) via a connector at a suitable position so that the outer diameter of the guide wire (1) is reduced, and the proximal end of the guide wire (1) can be inserted into a catheter to be deployed into the bodily cavity. The inflation port (4) is removed from the guide wire (2) via any suitable connector or by simply cutting it off.

The anchored guide wire (1) further includes an inline check valve (5) that enables the balloon (3) to be inflated, while preventing deflation. After a catheter is deployed using the guide wire (1), the guide wire can be removed by first deflating the balloon (3). This is done by deactivating the check valve (5) so as to allow the fluid to be released through a proximal outlet of the inner lumen of the guide wire (1). The check valve (5) is deactivated by releasing it or by detaching it at suitable point on the guide wire via a connector or by simply cutting it off. Once the balloon (3) is deflated, the guide wire (1) is pulled out of the body through the catheter.

Figure 3:
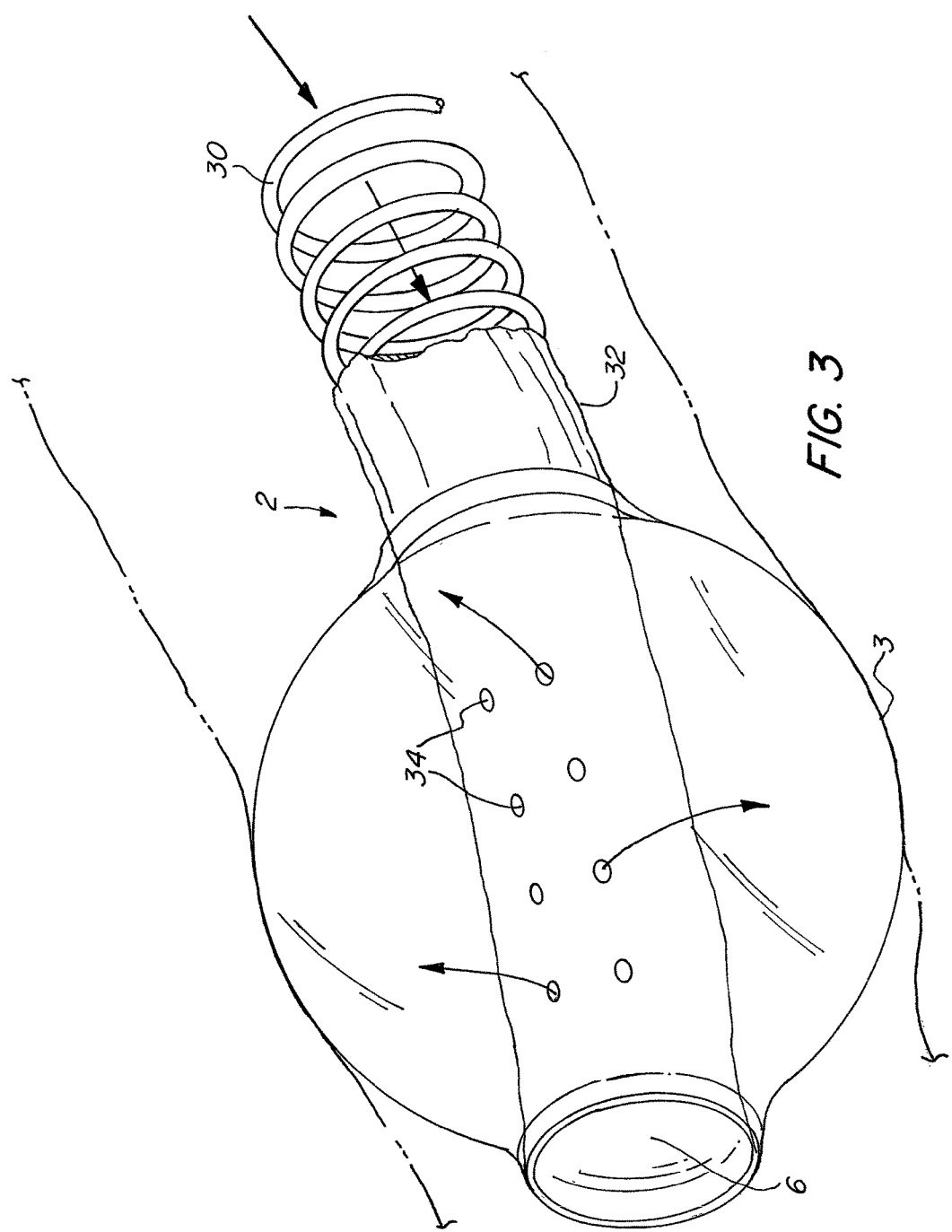
FIG. 3 is a perspective view of a distal end of the guide wire of FIG. 1.

FIG. 3 shows a perspective view of the distal end of the anchored guide wire. The elongated guide wire (2) includes a coil (30) with a coating (32) disposed on the coil. The guide wire (2) further includes the balloon (3) shown in an inflated configuration. The coating (32) creates a flexible fluidly isolated inner lumen (6) in the guide wire (2), through which the fluid is supplied from the pump (10) to the balloon (3). The balloon (3) is inflated though openings (34) in the coating (32) positioned inside the balloon (3).

Figure 4:
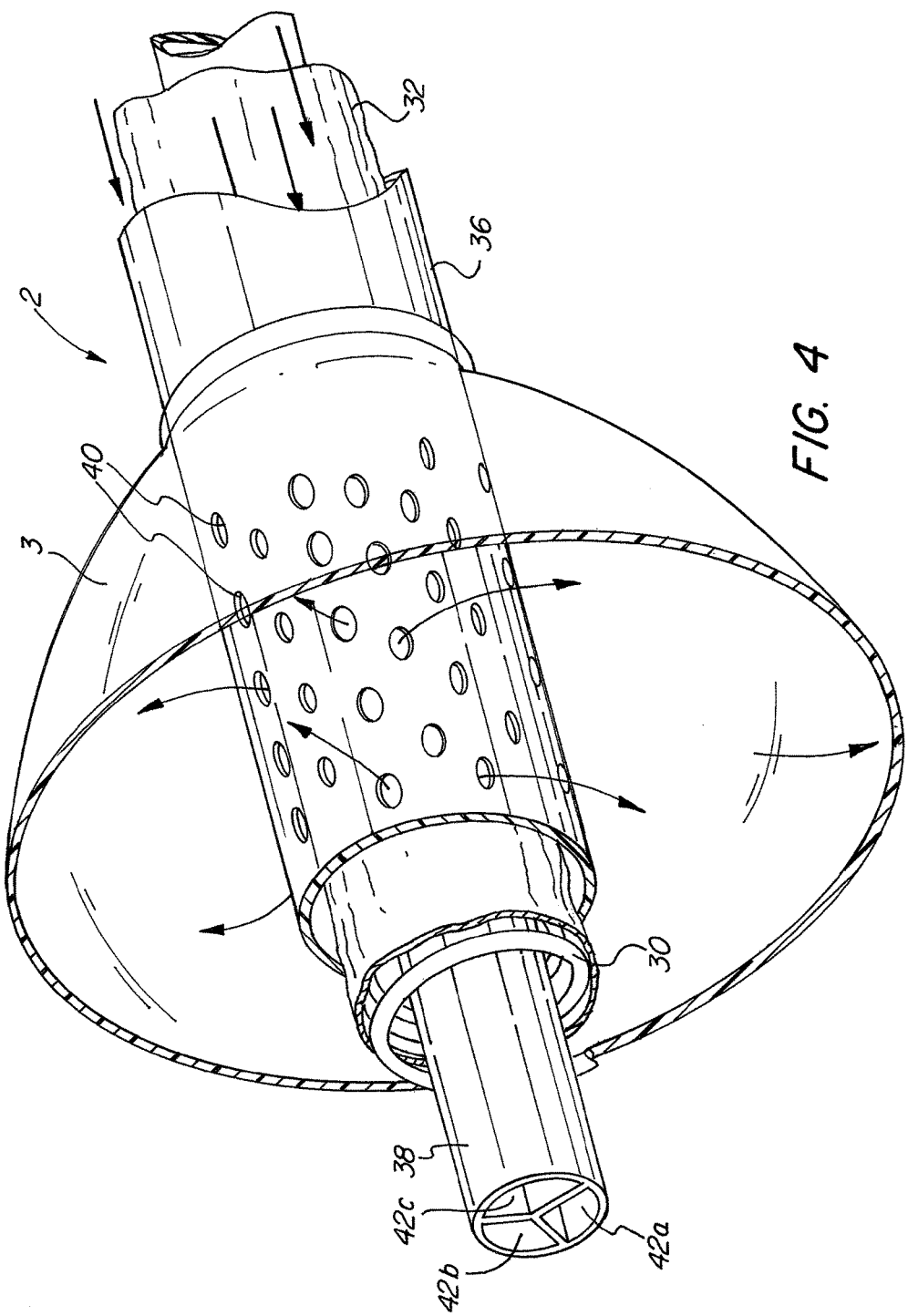
FIG. 4 is a perspective cross-sectional view of a distal end of the guide wire of FIG. 1.

FIG. 4 illustrates an alternative embodiment of the anchored guide wire. In this embodiment, the elongated guide wire (2) includes a coil (30) with a coating (32) disposed on the coil, an outer shaft (36) disposed on the coating (32), and an inner shaft (38) disposed inside the coil (30). The fluid is supplied from the pump (10) to the balloon (3) via the outer shaft (36), and the balloon (3) is inflated through the openings (40) provided in the outer shaft (36). The inner shaft (38) may be used to deliver any number of things to assist insertion and positioning of the anchored guide wire (1) within the bodily cavity. For example, additional lumens (42A, 42B, 42C), as shown in this figure, may be provided for introduction of various medical instruments to carry out various diagnostic or therapeutic procedures. The inner shaft (38) can also be used as a bypass channel to allow bodily fluids to flow through the guide wire, which is necessary in certain medical applications, e.g. pulmonology or cardiology.

Figure 19:
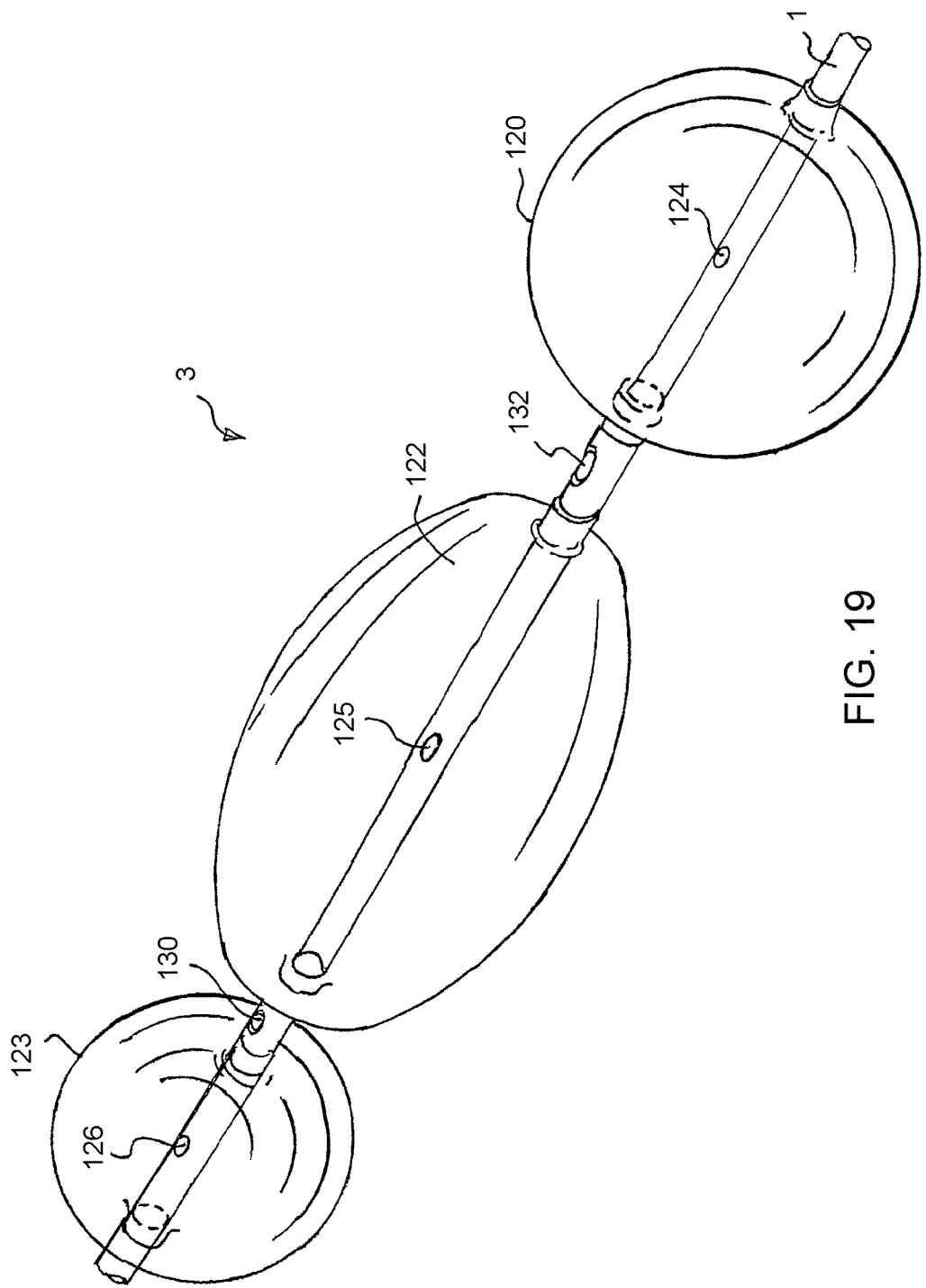
FIG. 19 is an enlarged perspective view of the guide wire of FIG. 1, with an expansion apparatus having a plurality of segments.

In certain embodiments, such as shown in FIG. 19, the expansion apparatus (3) includes a plurality of segments, for example, a proximal segment (120), a center segment (122), and a distal segment (123), and the guide wire (1) includes a plurality of inner lumens, each of the lumens being fluidly connected to a port (124, 125, 126) positioned inside each of the segments (120, 122, 123), through which the fluid is supplied from the pump to the plurality of segments. This allows for inflation of some segments of the expansion apparatus (3) separately from the other segments to aid in more precise positioning of the guide wire inside the patient's body.

Figure 5:
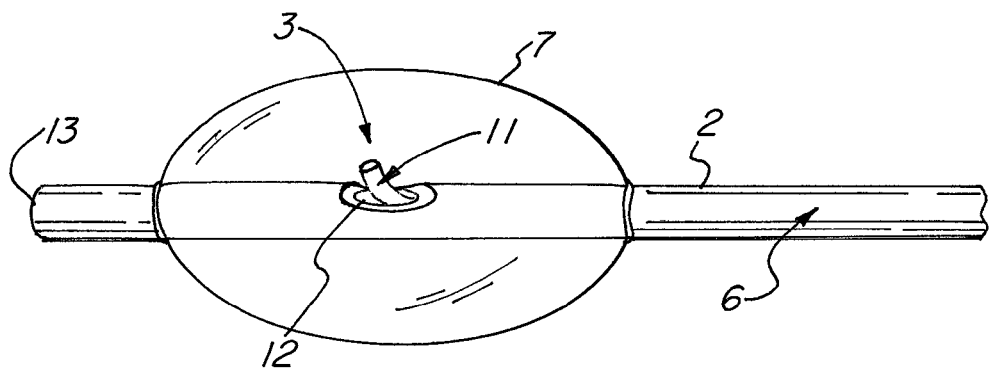
FIG. 5 is a partially schematic enlarged view of a distal end the guide wire of FIG. 1.

Referring to FIG. 5, the guide wire (1) is further provided with an imaging device (11) disposed in the elongated guide wire (2). In an advantageous embodiment, the imaging device (11) is a fiber optic image bundle. Two separate fiber optic bundles—an incoherent fiber bundle for illumination and a coherent fiber bundle for image—can also be used in accordance with the present invention. It should be noted that a suitable image sensor (e.g. CCD or CMOS) can be positioned at the tip of the imaging device (11), eliminating the need for coherent imaging fiber bundle, thus increasing the image quality and reducing cost. It should also be noted that other sources of illumination, such as light emitting diodes, can be employed.

The imaging device is introduced through the inner lumen (6) of the elongated guide wire (2). This way, the inner lumen (6) serves a dual purpose—it is used both for supply of fluid to inflate/deflate the expansion apparatus (3) and for visualization via the imaging device (11). As shown in FIG. 5, the elongated guide wire (2) includes an imaging device aperture (12). The imaging device aperture (12) is formed by a structural opening in the coil (30) forming the elongated guide wire (2). The aperture (12) may include an imaging marker to facilitate introduction of the imaging device (11). The imaging device (11) is deployed through the inner lumen (6) and the distal tip of the imaging device exits the aperture (12) for viewing surrounding tissue. The aperture may be positioned at any suitable location along the elongated guide wire (2). In some embodiments, the guide wire (2) is provided with a plurality of imaging device apertures (12) for better visualization of the surrounding area during the introduction of the guide wire into the patient's body.

In the embodiment illustrated in FIG. 5, the imaging device aperture (12) is positioned inside the balloon (3). The outer wall (7) of the balloon is made transparent when inflated, such that imaging is made possible from inside the balloon (3). Any suitable transparent material may be used in accordance with the invention. The imaging device (11) with an outer diameter less than the diameter of the inner lumen (6) is inserted towards the distal end of the guide wire (2) and is extended through the imaging device aperture (12). The imaging device (11) preferably includes a rotatable flexible distal tip that can be translated linearly or rotationally inside the balloon (3), thereby allowing for 360° visualization of the surrounding area. The imaging device aperture (12) can also serve as an inflation/deflation opening through which the fluid is supplied to/from the balloon (3).

The distal end of the elongated guide wire (2) preferably includes a transparent membrane (13) made out of any suitable material. The imaging device (11) is extended through the inner lumen (6) to the membrane (13), which allows for visualization of the area ahead of the balloon (3). In this way, the physician can be provided with illuminated light and direct visual feedback of the area ahead of the guide wire, along the sides of the balloon, and/or behind the balloon.

Figure 17:
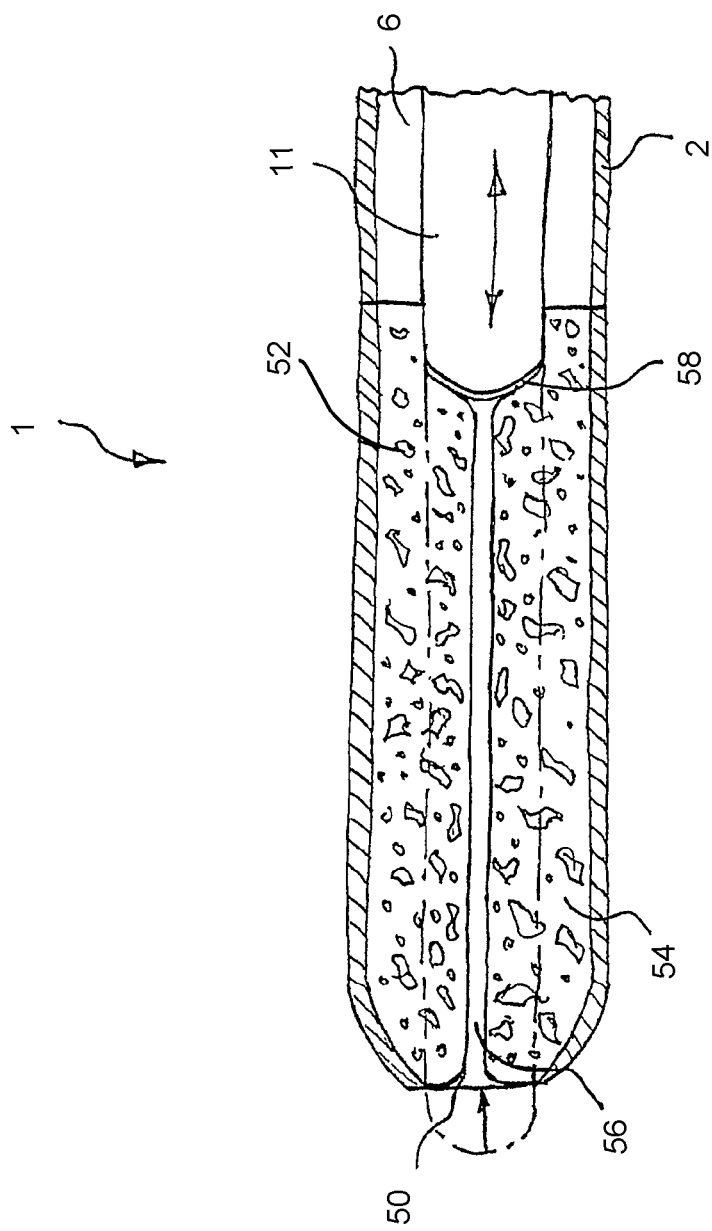
FIG. 17 is an enlarged cross-sectional view of a distal end of the guide wire of FIG. 1 with a cleaning device.

In another advantageous embodiment shown in FIG. 17, the inner lumen (6) of the elongated guide wire (2) has an opening (50) at the distal end, and the imaging device (11) is extended out of the opening (50) to visualize tissue in front of the guide wire (1). In this embodiment, the elongated guide wire (2) can also be provided with a cleaning device (52) at the distal tip for cleaning the imaging device (11). The cleaning device is made with any suitable type of material (54), such as textile bundle, and is affixed to an inner surface of the elongate guide wire (2) adjacent to the opening (50) at the distal end. The imaging device (11) is cleaned by moving it back and forth through a channel (56) in the textile bundle as shown in this figure, thus wiping a lens (58) of the imaging device.

The elongated guide wire (2) can also include a secondary inner lumen with an opening at a distal end. The secondary inner lumen serves as a passageway that allows the air and/or external fluid to move freely in both directions from each end of the expansion apparatus (3) when it is inflated, which is required in certain applications, such as bronchoscopy. Additionally, the secondary inner lumen can be used as a means for deploying various medical instruments into the bodily cavity for carrying out diagnostic or therapeutic procedures.

In some embodiments, the expansion apparatus (3) also includes openings to allow passage of external fluid through the apparatus. For example, as shown in FIG. 19, the expansion apparatus is provided with a plurality of segments (120, 122, 123), wherein some one of the segments (122) has two open ends (130, 132) creating an opening therethrough to allow passage of external fluids through the segment (122).

Figure 6A:
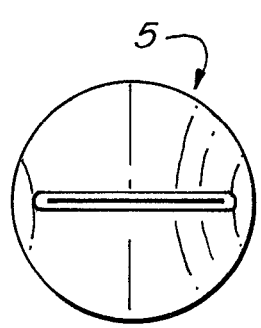
FIG. 6A is a front view of a check valve of the guide wire of FIG. 1.
Figure 6B:
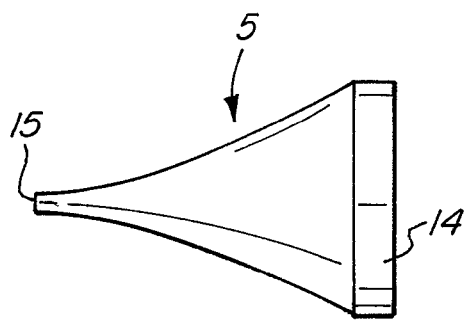
FIG. 6B is a side view of a check valve of the guide wire of FIG. 1.

FIGS. 6A and 6B illustrate a check valve (5) used to prevent the balloon from deflating in accordance with one embodiment of the guide wire. The check valve (5) has a cone-like shape, wherein a front part (14) has a circular periphery that fits the contours of the inner lumen (6), and a rear part (15) has two lips with an opening therebetween. The lips are capable of opening only in one direction. This way, the check valve allows for inflation of the balloon (3) when the fluid is supplied from the pump to the distal end of the guide wire, but prevents the deflation of the balloon (3), as the fluid cannot flow back through the valve (5) toward the proximal end of the guide wire.

Figure 7A:
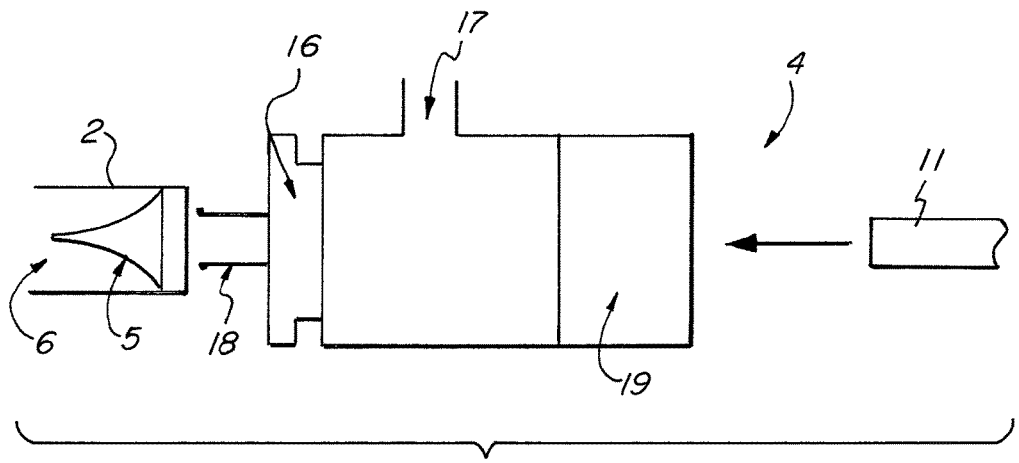
FIGS. 7A and 7B are partially schematic views of a connection port of the guide wire of FIG. 1.
Figure 7B:
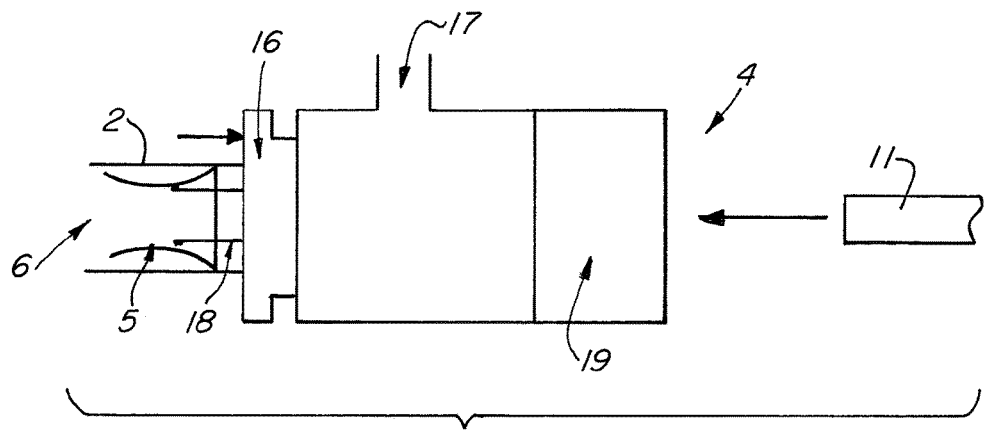

The check valve (5) is made with any suitable material, such as silicone or latex. The check valve (5) is inserted into the inner lumen (6) of the guide wire at the proximal end of the guide wire and is secured therein by any suitable means, such as glue. Because the valve is positioned inside the inner lumen (6) of the elongated guide wire (2), the outer diameter of the guide wire is not increased, which aids in minimally traumatic introduction of the guide wire into the patient's body. In should be understood that any other kind of a valve that allows flow of a fluid only in one direction can be used in accordance with the present invention FIGS. 7A and 7B illustrate an embodiment of the connection port (4) that facilitates inflation and deflation of the balloon (3) via the pump (10). In order to inflate the balloon (3), the proximal end of the elongated guide wire (2) is inserted into the connection port (4) and is secured in place by any suitable locking mechanism. In the embodiment shown in these figures, the locking mechanism is a push ring (16) that releasably secures the proximal end of the elongated guide wire (2) to the connection port (4). The connection port (4) also includes a side port (17) for inflation/deflation of the balloon (3). The side port (17) connects the inner lumen (6) of the guide wire with the pump, which supplies fluid to inflate the balloon (3).

The connection port (4) further includes a tube (18), which extends through the check valve (5) when the guide wire is connected to the connection port (4), as shown in FIG. 7B. The tube (18) facilitates deflation of the balloon (3) as it allows the fluid to flow through the valve (5) from the distal end to the proximal end of the guide wire. Thus, the tube (18) acts to disable the check valve (5) from stopping the back flow of fluid through the valve.

The connection port (4) also has an adapter (19) for accommodating insertion of the imaging device (11) into the anchored guide wire (1). The adapter (19) can be any suitable type, such as a silicone gasket, that provides an air/fluid tight connection between the imaging device (11) and the connection port (4). The imaging device (11) is inserted into the connection portion (4) through the adapter (19), and then is then passed through the elongated guide wire (2) via the inner lumen (6) connected to the connection port (4).

When in use, the proximal end of the guide wire (1) is first connected to the connection port (4) through the locking mechanism (16). The tube (18) is extended through the check valve (5) positioned in the inner lumen (2) of the elongated guide wire (2). The connection port (4) is connected to the pump (10) through a side port (17). The imaging device (11) is inserted into the connection port (4) through the adapter (19), and then is advanced through the inner lumen (6) toward the desired position inside the elongated guide wire (2). The guide wire is inserted into the patient's body and positioned at a target location with the aid of the imaging device.

Next, the balloon (3) is inflated by supplying fluid thereto from the pump (10) via the side port (17), thereby securing the guide wire at the target location. The imaging device (11) is then pulled out of the anchored guide wire (1), such that the distal end of the imaging device remains inside the connection port (4) to maintain the seal. The anchored guide wire (1) is disconnected from the connection port (4) by releasing the push ring (16). The tube (18) is pulled out of the check valve (5), enabling the valve to prevent the backflow of the fluid out of the balloon (3) and thereby preventing deflation of the balloon (3).

Then, a catheter or other desired instrument is introduced into the bodily cavity over the guide wire (1) to perform the desired medical procedure. Once the catheter is positioned inside the body, the connection port (4) is connected to the proximal end of the elongated guide wire (2) via the locking mechanism (16). Then tube (18) is inserted through the check valve (5), disabling the valve to allow the fluid to flow out of the balloon (3), thereby deflating it. Once the balloon (3) is fully deflated, the anchored guide wire (1) is pulled out of the patient's body.

FIGS. 9-15 illustrate a method of deployment of a catheter into a bodily cavity by utilizing the anchored guide wire (1) in accordance with the present invention.

Figure 9:
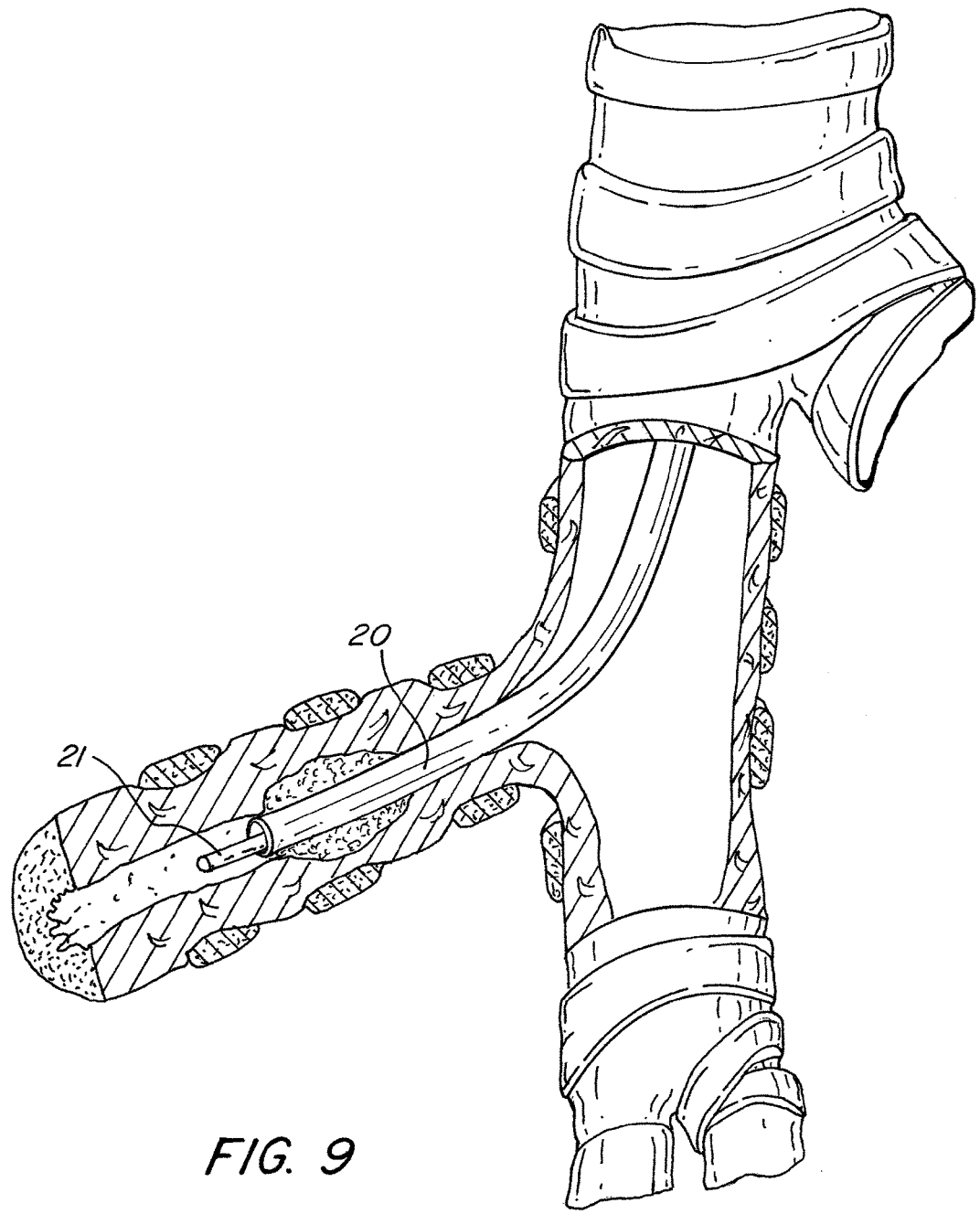
FIGS. 9-15 are views of the guide wire of FIG. 1 being operated in a bodily cavity.
Figure 10:
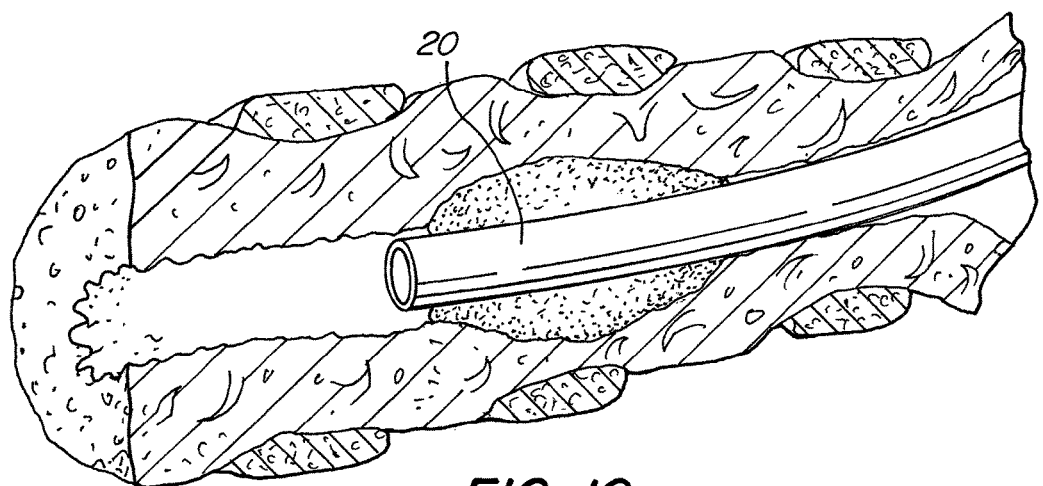

As shown in FIG. 9, a catheter (20) is first introduced into a desired location within a patient's body. Any known type of the catheter may be used in accordance with the present invention. In an advantageous embodiment, the guide wire is introduced into the body via a steerable catheter having an imaging system (21). In other preferred embodiments, a catheter system with radio opaque markers may be used for indirect imaging. After the steerable catheter (20) is positioned at the target site, the imaging system (21) is pulled out of the catheter's inner lumen, as shown in FIG. 10.

Figure 11:
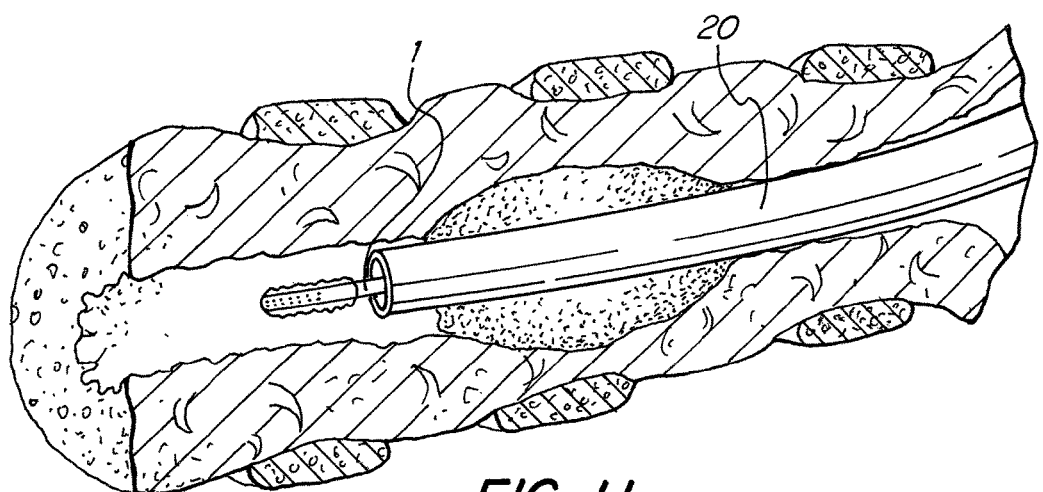

As illustrated in FIG. 11, the anchored guide wire (1) is then inserted into the bodily cavity through the inner lumen of the catheter (20). In an advantageous embodiment, the anchored guide wire (1) has markings on the proximal end of the wire that indicate the exact length of the wire to be inserted into the catheter lumen. The anchored guide wire (1) is inserted such that the distal end of the wire is protracted out of the inner lumen of the catheter (20) and is extended into the bodily cavity.

Figure 12:
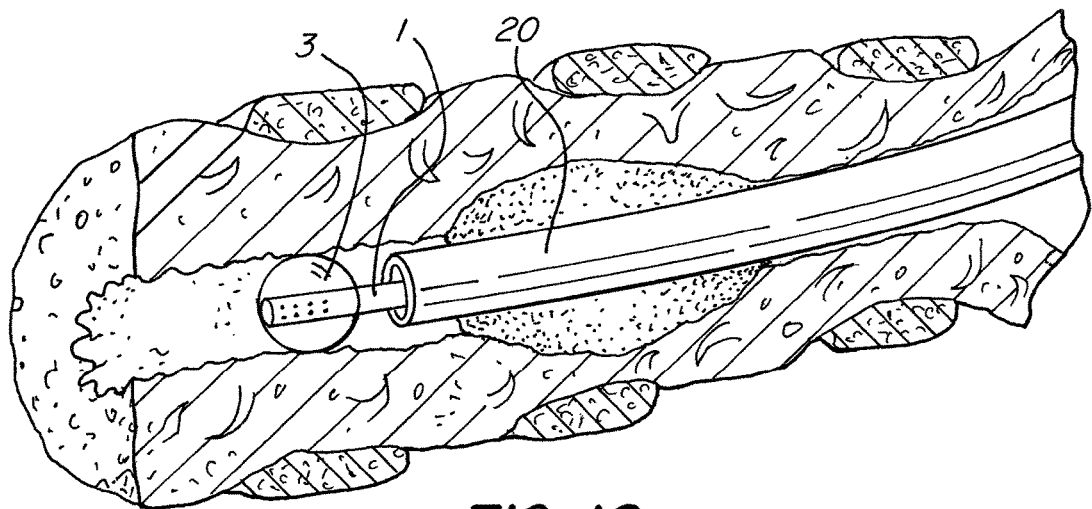

Referring to FIG. 12, the expansion apparatus, such as an inflatable balloon (3), positioned at the distal end of the anchored guide wire (1) is then inflated by using a pump connected to the guide wire via a connection port, as described above. A check valve positioned at the proximal end of the guide wire (1) operates to prevent the balloon (3) from deflating when it is disconnected from the pump.

Figure 13:
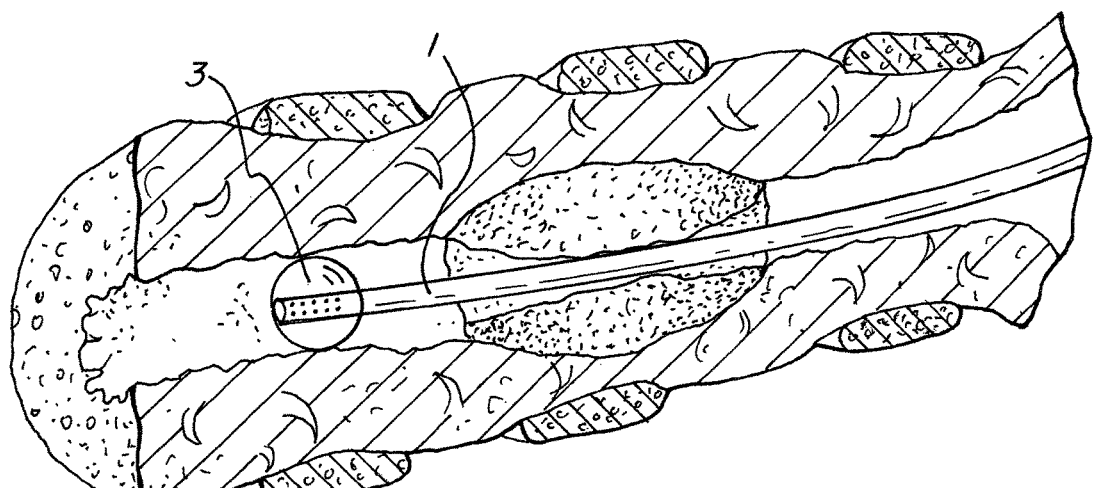

After the guide wire (1) is disconnected from the pump, it is detached from the connection port via a releasable connection means, as described above. It should be noted that the guide wire can also be disconnected by simply cutting the proximal end of the guide wire (1), leaving the check valve in place. The check valve is positioned in line with the inner lumen of the guide wire (1), and it allows the balloon (3) to stay inflated. The catheter (20) is then removed from the bodily cavity, as shown in FIG. 13.

Figure 14:
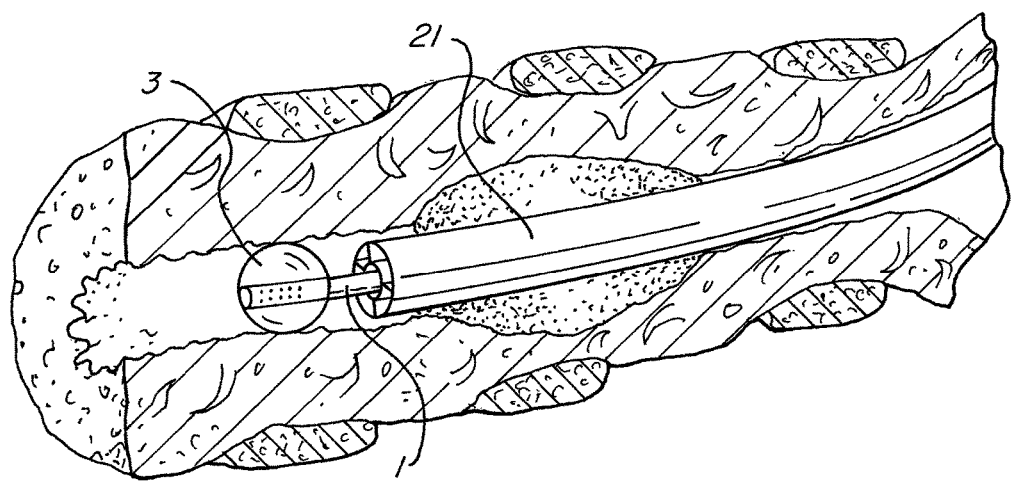

Next, the proximal end of the guide wire (1) is inserted into a lumen of another catheter (22) that will be used to perform a desired medical procedure. In a preferred embodiment of the present invention, a resector balloon system described in U.S. patent application Ser. No. 12/269,495 is used. As illustrated in FIG. 14, the catheter (22) is advanced over the guide wire (1) until only the distal end of the guide wire (1) extends out of the lumen of the catheter (22). The appropriate positioning of the catheter (22) may be determined by aligning markings on the proximal end of the guide wire (1) with the proximal end of the catheter's inner lumen. The step may be monitored under fluoroscopy to ensure that the balloon (3) has not moved out of position. An imaging system may also be employed during this procedure through one of the other inner channels provided in the catheter (22).

Figure 15:
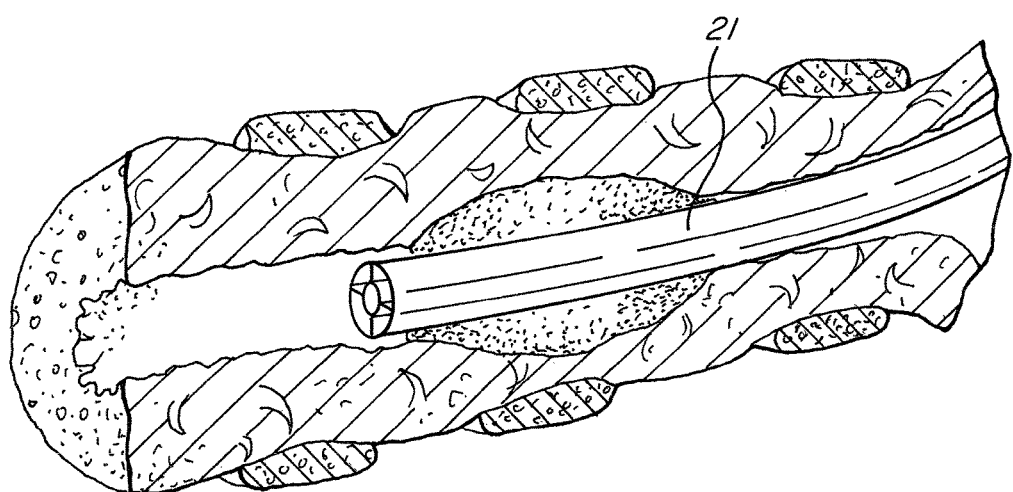

Once the catheter (22) is deployed to the target site, the balloon (3) is deflated. This is done by connecting the guide wire (1) to the connection port and inserting the tube through the check valve to allow the fluid to flow out of the balloon, as described above. However, this may also be done by cutting off the check valve section of the guide wire (1). The guide wire (1) is then pulled out through the inner lumen of the catheter (12) out of the patient's body, as shown in FIG. 15, leaving the catheter (22) in the bodily cavity. Next, the catheter (22) is utilized to perform any desired medical procedure, such as the resection procedures described in U.S. patent application Ser. No. 12/269,495.

It would be appreciated by those skilled in the art that various changes and modifications can be made to the illustrated embodiment without departing from the spirit of the present invention. All such modifications and changes are intended to be covered hereby.

What is claimed is:

1. A method of using a guide wire in a bodily cavity, comprising the steps of:
    inserting into a bodily cavity an elongated guide wire having
        a balloon at a distal end of the guide wire;
        a fiber mesh disposed over the balloon and affixed thereto; and
        a lumen in fluid communication with the balloon;
    advancing the distal end of the guide wire through the bodily cavity until the balloon reaches an anchoring position;
    supplying fluid though the lumen to the balloon until the balloon is inflated such that the balloon with the fiber mesh exerts pressure on the wall of the bodily cavity to retain the balloon in the anchoring position;
    advancing a medical device over the elongated guide wire through the bodily cavity while the balloon is inflated until the medical device reaches a desired position;
    deflating the balloon; and
    withdrawing the guide wire through the medical device and out of the bodily cavity.

2. The method of claim 1, wherein the guide wire comprises a coiled wire.

3. The method of claim 2, wherein the guide wire comprises a coiled stainless steel wire coated with polyethylene.

4. The method of claim 1, wherein the elongated guide wire has a check valve disposed in the lumen at a proximal end thereof to maintain the inflation of the balloon, and wherein the step of deflating the balloon comprises disabling the check valve to release fluid from the balloon.

5. The method of claim 4, wherein the check valve comprises silicone.

6. The method of claim 4, wherein the check valve has a proximal part with a periphery corresponding to the lumen, and a distal part comprising two lips that allow the supply of fluid toward the distal end of the guide wire and prevent the flow of fluid back toward the proximal end of the guide wire by opening only in one direction.

7. The method of claim 6, wherein the step of supplying fluid through the lumen to the balloon comprises supplying the fluid through a connection port connected to the proximal end of the guide wire, wherein the method further comprises the step of disconnecting the proximal end of the guide wire from the inflation port prior to the step of advancing a medical device over the elongated guide wire, and wherein the step of disabling the check valve comprises reconnecting the proximal end of the elongated guide wire to the connection portion such that a tube of the connection port extends through the check valve.

8. The method of claim 1, wherein the step of advancing a medical device over the elongated guide wire comprises sliding a catheter over the elongated guide wire.

9. The method of claim 1, wherein the step of supplying fluid through the lumen includes supplying the fluid via a fluid source having at least one sensor for measuring at least one parameter and a processor for controlling the supply of fluid based on the at the least one measured parameter.

10. The method of claim 9, wherein the fluid source comprises an electropneumatic pump.

11. The method of claim 1, further comprising the step of visualizing tissue in the bodily cavity by advancing an imaging device through the lumen.

12. The method of claim 11, wherein the step of supplying fluid through the lumen to the balloon comprises supplying the fluid through a connection port connected to the proximal end of the guide wire, wherein the connection port includes an adapter through which the imaging device is inserted into the lumen.

13. The method of claim 12, wherein the adaptor comprises a silicone gasket.

14. The method of claim 11, wherein the balloon is transparent, and wherein the step of visualizing tissue comprises extending a distal tip of the imaging device through an aperture positioned inside the balloon.

15. The method of claim 11, wherein the step of visualizing tissue comprises viewing the tissue in front of the guide wire with the imaging device through a transparent membrane positioned at a distal end of the elongated guide wire.

16. The method of claim 11, wherein the step of visualizing tissue comprises extending a distal tip of said imaging device through an opening at a distal end of said elongated guide wire to visualize tissue in front of the guide wire.

17. The method of claim 16, further comprising the step of cleaning the imaging device via a cleaning device positioned in the opening at the distal end of said elongated guide wire.

18. The method of claim 1, further comprising the step of using at least one imaging marker to position the balloon within the bodily cavity.

19. The method of claim 1, wherein the balloon has a distal tip with an opening therein and said elongated guide wire has a second lumen connected to said opening, further comprising the step of passing bodily fluids through the second opening and out the second lumen of the guide wire.

20. The method of claim 1, wherein:
    the balloon comprises a plurality of segments;
    the elongated guide wire comprises a plurality of lumens; and
    the step of supplying fluid to the expansion apparatus comprises supplying fluid to the plurality of segments such that at least one of the segments is inflated separately from at least one other of the segments.

* * * * *